(12) United States Patent
Sugiyama et al.

(10) Patent No.: US 11,395,999 B2
(45) Date of Patent: Jul. 26, 2022

(54) METHOD FOR PRODUCING LIPOSOME AND APPARATUS FOR PRODUCING LIPOSOME

(71) Applicant: FUJIFILM Corporation, Tokyo (JP)

(72) Inventors: Susumu Sugiyama, Ashigarakami-gun (JP); Naoki Yamada, Ashigarakami-gun (JP); Shigehisa Sugiyama, Ashigarakami-gun (JP); Yohei Okubo, Minami-ashigara (JP); Takashi Sasaki, Minami-ashigara (JP); Tetsu Ishiguro, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/868,092

(22) Filed: Jan. 11, 2018

(65) Prior Publication Data

US 2018/0133676 A1    May 17, 2018

Related U.S. Application Data

(60) Division of application No. 15/625,020, filed on Jun. 16, 2017, which is a continuation of application No. PCT/JP2015/085456, filed on Dec. 18, 2015.

(30) Foreign Application Priority Data

Dec. 19, 2014  (JP) ................................. 2014-257283

(51) Int. Cl.
  *B01J 13/04*  (2006.01)
  *A61K 9/127*  (2006.01)
  (Continued)

(52) U.S. Cl.
  CPC .............. *B01J 13/04* (2013.01); *A61K 9/127* (2013.01); *A61K 9/1271* (2013.01);
  (Continued)

(58) Field of Classification Search
  CPC ................................ B01J 13/04; B01F 15/065
  (Continued)

(56) References Cited

U.S. PATENT DOCUMENTS

| 431,372 A | * | 7/1890 | Medlin | ................... | A23G 9/12 |
| | | | | | 165/109.1 |
| 444,345 A | | 1/1891 | Gabbett et al. | | |

(Continued)

FOREIGN PATENT DOCUMENTS

| CA | 747937 A | 12/1966 |
| JP | 54-41279 A | 4/1979 |

(Continued)

OTHER PUBLICATIONS

Extended European Search Report, dated Nov. 15, 2017, for European Application No. 15870075.7.

(Continued)

*Primary Examiner* — Marc C Howell
(74) *Attorney, Agent, or Firm* — Birch, Stewart, Kolasch & Birch, LLP

(57) ABSTRACT

Disclosed herein are a method for producing a liposome which is capable of reducing the facility costs and also capable of rapid desolvation, and an apparatus for producing a liposome which is for use in the above-mentioned method. Provided is a method for producing a liposome, including a stirring step of stirring a mixed liquid containing an oil phase in which at least one lipid is dissolved in an organic solvent and a water phase, and an evaporating step of evaporating an organic solvent from the mixed liquid, in which the condensed organic solvent is removed by passing a gas having a temperature not higher than the dew point of the solvent in the evaporating step.

20 Claims, 2 Drawing Sheets

(51) Int. Cl.

| | |
|---|---|
| *B01F 23/41* | (2022.01) |
| *B01F 25/50* | (2022.01) |
| *B01F 27/27* | (2022.01) |
| *B01D 1/00* | (2006.01) |
| *B01D 5/00* | (2006.01) |
| B01F 101/22 | (2022.01) |

(52) U.S. Cl.
CPC ............ *A61K 9/1277* (2013.01); *B01D 1/00* (2013.01); *B01D 5/006* (2013.01); *B01F 23/41* (2022.01); *B01F 25/50* (2022.01); *B01F 27/27* (2022.01); *B01F 23/4145* (2022.01); *B01F 2101/22* (2022.01)

(58) Field of Classification Search
USPC ......................................................... 366/149
See application file for complete search history.

(56) References Cited

U.S. PATENT DOCUMENTS

| | | | |
|---|---|---|---|
| 718,227 A | 1/1903 | Stetson | |
| 742,712 A | 10/1903 | Morris | |
| 780,260 A | 1/1905 | Beemer | |
| 1,156,606 A * | 10/1915 | Lawrie | C01F 7/24 366/140 |
| 1,420,210 A * | 6/1922 | Paulus | B01F 7/04 127/1 |
| 1,645,614 A | 10/1927 | Monahan | |
| 1,961,903 A * | 6/1934 | McKee | C10M 5/00 165/109.1 |
| 2,703,304 A * | 3/1955 | Paladino | B01F 7/22 366/102 |
| 3,067,988 A | 12/1962 | Rodoz | |
| 3,128,084 A | 4/1964 | Castor | |
| 3,424,733 A * | 1/1969 | Pollock | B01J 19/18 366/149 |
| 3,765,656 A | 10/1973 | Tofaute | |
| 3,951,386 A * | 4/1976 | Small | B01F 15/00207 366/142 |
| 4,224,179 A | 9/1980 | Schneider | |
| 4,235,871 A | 11/1980 | Papahadjopoulos et al. | |
| 4,752,425 A | 6/1988 | Martin et al. | |
| 4,781,871 A | 11/1988 | West et al. | |
| 4,895,452 A | 1/1990 | Yiournas et al. | |
| 5,000,887 A | 3/1991 | Tenzel et al. | |
| 5,013,497 A | 5/1991 | Yiournas et al. | |
| 5,094,785 A | 3/1992 | Law et al. | |
| 5,096,629 A | 3/1992 | Nanba et al. | |
| 5,194,188 A | 3/1993 | Guitierrez | |
| 5,234,636 A | 8/1993 | Grollier et al. | |
| 5,292,194 A * | 3/1994 | Gabor | B01F 7/00241 366/262 |
| 5,540,936 A | 7/1996 | Coe et al. | |
| 5,582,484 A * | 12/1996 | Asa | B01F 3/0807 366/149 |
| 5,653,996 A | 8/1997 | Hsu | |
| 5,700,482 A | 12/1997 | Frederiksen et al. | |
| 5,702,722 A | 12/1997 | Tournier et al. | |
| 5,891,467 A | 4/1999 | Willis | |
| 5,932,562 A | 8/1999 | Ostlund, Jr. | |
| 5,993,850 A | 11/1999 | Sankaram et al. | |
| 6,599,005 B2 * | 7/2003 | Van Der Wel | B01F 7/00208 366/143 |
| 6,989,042 B2 | 1/2006 | Dry | |
| 7,083,572 B2 | 8/2006 | Unger et al. | |
| 8,354,064 B2 | 1/2013 | Nakamura et al. | |
| 8,951,450 B2 | 2/2015 | Shimizu et al. | |
| 2002/0039596 A1 | 4/2002 | Hartounian et al. | |
| 2002/0041895 A1 | 4/2002 | Gregoriadis et al. | |
| 2002/0119188 A1 | 8/2002 | Niemiec et al. | |
| 2003/0094715 A1 | 5/2003 | Suzuki et al. | |
| 2005/0008746 A1 | 1/2005 | Beck et al. | |
| 2007/0182040 A1 | 8/2007 | Suzuki | |
| 2010/0080077 A1 * | 4/2010 | Coy | B01F 5/02 366/137 |
| 2010/0316696 A1 | 12/2010 | Wiggenhorn et al. | |
| 2011/0250264 A1 | 10/2011 | Schutt et al. | |
| 2012/0081990 A1 | 4/2012 | Murata | |
| 2013/0095043 A1 | 4/2013 | Burdinski et al. | |
| 2013/0177633 A1 | 7/2013 | Schutt et al. | |
| 2014/0004173 A1 | 1/2014 | Hartounian et al. | |

FOREIGN PATENT DOCUMENTS

| | | |
|---|---|---|
| JP | 64-9931 A | 1/1989 |
| JP | 2-502460 A | 8/1990 |
| JP | 9-503225 A | 3/1997 |
| JP | 10-502667 A | 3/1998 |
| JP | 2001-505224 A | 4/2001 |
| JP | 2001-522870 A | 11/2001 |
| JP | 2002-516260 A | 6/2002 |
| JP | 2005-505645 A | 2/2005 |
| JP | 2010-285438 A | 12/2010 |
| JP | 2011-5349 A | 1/2011 |
| JP | 2012-240010 A | 12/2012 |
| JP | 2013-529677 A | 7/2013 |
| WO | WO 01/83594 A1 | 11/2001 |

OTHER PUBLICATIONS

International Search Report for PCT/JP2015/085456 dated Mar. 15, 2016.
Japanese Office Action and English translation, dated Nov. 14, 2017, for Japanese Application No. 2014-257283.
Notification Concerning Transmittal of International Preliminary Report on Patentability; International Preliminary Report on Patentability; Notification of Transmittal of Translation of the international Preliminary Report on Patentability; and English Translation of Written Opinion of the International Searching Authority dated Jun. 29, 2017, issued in PCT/JP2015/085456 (Forms PCT/IB/326, PCT/IB/373, PCT/IB/338 and PCT/ISA/237).
Office Action dated Dec. 28, 2017 in U.S. Appl. No. 15/625,020.
Ohe, "Theory and Calculation of Phase Equilibrium for the Separation", Kodansha Ltd., 2012, pp. 75-76.
Ohe, "Vapor-Liquid Equilibrium Data Collection", Kodansha Ltd., 1988, p. 216.
Written Opinion of the International Searching Authority for PCT/JP2015/085456 (PCT/ISA/237) dated Mar. 15, 2016.
IPMS Inc. Stirring Revolution. Copyright 2014. Retrieved Dec. 25, 2017. pp. 1-2. <https://www.aaamachine.com/exhibition/20160503/pdf/Brachure_M-Revo_AAASaveEnergy_english-20160429.pdf>. (Year: 2014).
European Office Action for corresponding European Application No. 15870075.7, dated Feb. 12, 2020.
Office Action dated Jul. 25, 2018 in U.S. Appl. No. 15/625,020.
U.S. Office Action, dated Dec. 27, 2019, far U.S. Appl. No. 15/625,020.
European Office Action, dated Feb. 24, 2021. for European Application No. 15870075.7.
Office Action dated Aug. 10, 2021 in U.S. Appl. No. 15/625,020.
U.S. Office Action, dated Jun. 18, 2019, for U.S. Appl. No. 15/625,020.

* cited by examiner

METHOD FOR PRODUCING LIPOSOME AND APPARATUS FOR PRODUCING LIPOSOME

CROSS-REFERENCE TO RELATED APPLICATIONS

The present application is a division of co-pending U.S. patent application Ser. No. 15/625,020 filed Jun. 16, 2017, which is a continuation of International Application PCT/JP2015/085456 filed on Dec. 18, 2015, which claims priority under 35 U.S.C. § 119 of Japanese Patent Application No. 257283/2014 filed on Dec. 19, 2014, all of which are hereby expressly incorporated by reference into the present application

BACKGROUND OF THE INVENTION

1. Field of the Invention

The present invention relates to a method for producing a liposome and an apparatus for producing a liposome. Specifically, the present invention relates to a method for producing a liposome which can be suitably used for pharmaceutical applications and an apparatus for producing such a liposome.

2. Description of the Related Art

A liposome (hereinafter, also referred to as lipid vesicle) is a closed vesicle formed of a lipid bilayer membrane using lipids, and has an aqueous solution (outer water phase) in which liposomes are dispersed and a water phase (inner water phase) within the space of the closed vesicle. Liposomes have been studied for a variety of applications such as immune sensors, artificial red blood cells, and carriers of drug delivery systems taking advantage of the features such as barrier capacity, compound retention capacity, biocompatibility, the degree of freedom of setting the particle size, ready biodegradability, and surface-modifying properties. As for the application of a carrier, liposomes can encapsulate water-soluble compounds, lipophilic low-molecular weight and high-molecular weight materials, and a wide range of materials. As an example of the method for producing a liposome, there is a method in which a water phase and an oil phase are stirred and emulsified in a stirring apparatus, followed by desolvation.

JP2005-505645A (paragraph 0074) discloses that an emulsion is prepared by stirring a dispersion system in which an oil based solution A is added to an aqueous solution B, flushing the dispersion system with nitrogen, and then maintaining the dispersion system at 55° C. for 60 minutes to evaporate the residual methylene chloride. WO01/083594A (Example 9) discloses that an emulsion is poured into a cylindrical airtight container and stirred at room temperature at 400 rpm while a nitrogen gas is simultaneously passed through the hollow fiber for one hour to remove methylene chloride from the container, thereby obtaining microsphere particles. JP2010-285438A (paragraph 0149), JP1997-503225A (JP-H09-503225A) (claim 4), and JP1990-502460A (JP-H02-502460A) also disclose that the produced emulsion is subjected to removing of a solvent. Similarly, JP1989-009931A (JP-H01-009931A) (Example 3), JP2002-516260A (Example 4), JP2013-529677A (paragraph 0103), and JP2001-505224A (Example 3) also disclose that the produced emulsion is subjected to removing of a solvent.

SUMMARY OF THE INVENTION

In the preparation of liposomes, it is important to rapidly remove the solvent in the liquid by a desolvation step in order to prevent re-coalescence of the dispersion miniaturized in an emulsifying step and to stabilize the particle size. In order to achieve the desolvation, it is necessary to supply heat from an external by a hot water jacket or the like. However, if the liquid preparation scale becomes larger, the heat transfer area per volume of the liquid becomes smaller, so the heat supply becomes insufficient and the evaporation rate will decrease. As a result, the re-coalescence of the dispersion proceeds and therefore it becomes impossible to reduce the particle size of the liposomes.

In order to achieve rapid desolvation, it is necessary to discharge the evaporated solvent gas and water vapor to the exterior of the desolvation vessel in a gaseous state at a rapid rate. For this purpose, however, a large amount of clean air or nitrogen (carrier gas) is required and the capital investment burden to supply them becomes excessive, which was an obstacle to practical use. In order to reduce the amount of carrier gas being used, it is necessary to heat the carrier gas to thereby increase the saturated vapor volume. However, it has not been possible to solve the problem because it was necessary to invest in the heating equipment of the carrier gas.

It is an object of the present invention to provide a method for producing a liposome which is capable of reducing the facility costs and also capable of rapid desolvation, and an apparatus for producing a liposome for use in the above-mentioned method.

As a result of extensive studies to solve the above-mentioned problems, the present inventors have found that, in a method for producing a liposome, including a stirring step of stirring a mixed liquid containing an oil phase and a water phase and an evaporating step of evaporating an organic solvent from the mixed liquid, desolvation can be rapidly achieved by passing a gas at a temperature not higher than the dew point of the solvent in the evaporating step to thereby remove the condensed organic solvent. The present invention has been completed based on such findings. That is, according to the present invention, the following will be provided.

(1) A method for producing a liposome, comprising a stirring step of stirring a mixed liquid containing an oil phase in which at least one lipid is dissolved in an organic solvent and a water phase, and an evaporating step of evaporating an organic solvent from the mixed liquid, in which the condensed organic solvent is removed by passing a gas having a temperature not higher than the dew point of the solvent in the evaporating step.

(2) The method for producing a liposome according to (1), in which the stirring step and the evaporating step are carried out in a tank, and the ratio A/B of length A of the widest portion of the liquid horizontal plane of the mixed liquid in the tank at the start of the evaporating step to length B of the deepest portion of the liquid depth is 2 or more.

(3) The method for producing a liposome according to (1) or (2), in which the stirring step and the evaporating step are carried out in a tank, and the ratio C/D of length C of the widest portion of the horizontal plane of the gas space in the tank at the start of the evaporating step to length D of the longest portion of the height of the gas space is 3 or more, where the gas space refers to a space occupied by the gas flowing in a horizontal direction on the liquid surface.

(4) The method for producing a liposome according to any one of (1) to (3), in which the capacity of the tank is 10 L or more and 100 L or less.

(5) The method for producing a liposome according to any one of (1) to (4), in which the evaporating step is carried out by stirring using a centrifugal stirrer.

(6) The method for producing a liposome according to any one of (1) to (5), in which the centrifugal stirrer has 2 to 10 discharge ports, the discharge rate coefficient indicated by total opening area of the discharge ports×circumferential length is 60 cm$^3$ to 6,000 cm$^3$, and the rotation speed of the centrifugal stirrer is 100 to 1,500 rpm.

(7) The method for producing a liposome according to any one of (1) to (6), in which in the evaporating step, the gas is sucked into the container from the central portion of the upper portion of the container, and the gas and the condensed organic solvent are discharged from the peripheral portion of the upper portion of the container.

(8) An apparatus for producing a liposome, comprising a tank, a stirrer, and a jacket, in which the cross-section of the space in the tank has a circular shape, the size of the circle in the cross-section is variable depending on the height of the tank, the stirrer is inserted into the tank from the center of the lid at the top of the tank, the jacket is provided around the tank to control the temperature in the tank, one or more inlet ports for sucking gas into the tank are provided at the central portion of the lid at the top of the tank, and one or more outlet ports for discharging the gas and condensed organic solvent from the tank are provided at the peripheral portion of the lid at the top of the tank.

(9) The apparatus for producing a liposome according to (8), in which the capacity of the tank is 10 L or more and 100 L or less.

According to the present invention, it is possible to reduce the used amount of carrier air (nitrogen or clean air) required for desolvation and reduce the cost of the equipment. Further, according to the present invention, it is possible to achieve efficient heat balance and rapid desolvation by recovering the latent heat of evaporation by mist generation.

DESCRIPTION OF THE PREFERRED EMBODIMENTS

Figure 1:
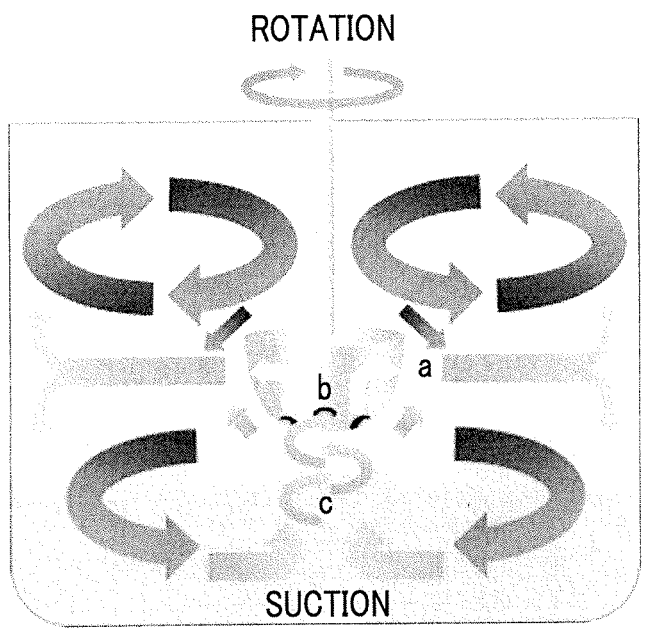
FIG. 1 shows a configuration example of a centrifugal stirrer.

The term "step" used herein includes not only an independent step, but also a step which may not be clearly separated from another step, insofar as an expected effect of the step can be attained.

The numerical ranges shown with "to" in the present specification means ranges including the numerical values indicated before and after "to" as the minimum and maximum values, respectively.

In referring herein to a content of a component in a composition, in a case where plural substances exist corresponding to a component in the composition, the content means the total amount of the plural substances existing within the composition, unless otherwise specified.

Hereinafter, the present invention will be described in detail.

The method for producing a liposome according to the present invention is a method for producing a liposome, including a stirring step of stirring a mixed liquid containing an oil phase in which at least one lipid is dissolved in an organic solvent and a water phase, and an evaporating step of evaporating an organic solvent from the mixed liquid, in which the condensed solvent is removed by passing a gas having a temperature not higher than the dew point of the solvent in the evaporating step.

As a basic idea of the drying technique and the desolvation technique, it is a principle to discharge the evaporated solvent gas and water vapor out of the system by blowing a carrier gas in an amount and at a temperature sufficient to maintain such evaporated solvent gas and water vapor below a saturated vapor volume thereof. There is no known system for desolvation under the conditions above the saturated vapor volume. Therefore, the method for producing a liposome according to the present invention, which includes the removal of the condensed organic solvent by passing a gas having a temperature not higher than the dew point of the solvent, is based on the fact that the idea itself is novel. The reason why the removal of the condensed organic solvent has not been conceived until now is thought to be due to the fact that there was a concern that the efficiency of desolvation would be significantly lowered because the condensed solvent or water would turn into water droplets and be refluxed onto the inner wall of the container or exhaust air duct if it was not discharged quickly out of the container. As described above, the idea of the present invention is contradictory to the basic conventional principle, and thereby achieving rapid desolvation is a completely unexpected advantageous effect.

That is, according to the present invention, it is possible to discharge the solvent out of the system with a smaller amount of carrier gas, due to it not being restricted by the saturated vapor pressure by physically discharging a portion or all of the solvent gas and water vapor on a carrier gas while condensing (mist generation) at a dew point or less. In this case, the latent heat absorbed once the solvent and water are evaporated is recovered by the heat generated during the mist generation, so that rapid desolvation can be achieved by a smaller heat supply of the jacket. Further, the heating equipment of the carrier gas also becomes unnecessary.

(Liposome)

Liposome is a lipid vesicle formed from a lipid bilayer containing lipid molecules. Specifically, the liposome refers to a vesicle containing a closed lipid having a space separated from the external environment by a lipid bilayer formed based on the polarity of the hydrophobic groups and hydrophilic groups of the lipid molecules. The liposome is a closed vesicle formed of a lipid bilayer membrane using lipids, and has a water phase (inner water phase) within the space of the closed vesicle. The inner water phase contains water and the like. The liposome may be single lamellar (monolayer lamellar, unilamellar, or single bilayer membrane) or multilayered lamellar (multilamellar, which is an onion-like structure having multiple bilayer membranes where individual layers are compartmented by water-like layers). In the present invention, a monolayer lamellar liposome is preferred from the viewpoint of safety and stability in pharmaceutical applications.

The liposome is preferably a liposome capable of encapsulating a drug and is not particularly limited in terms of form. The "encapsulating" means taking a form in which a drug is contained in an inner water phase and a membrane with respect to the liposome. For example, the liposome may be a form where a drug is encapsulated within a closed space formed of a membrane, a form where a drug is included in the membrane itself, or a combination thereof.

The size (average particle size) of the liposome is not particularly limited and is preferably 100 nm or less, more preferably 30 to 70 nm, still more preferably 40 to 60 nm, and particularly preferably 40 to 55 nm. The liposome is preferably in the form of a spherical shape or a shape close thereto. In the present invention, the "average particle size" means a volume average value of the diameters of liposomes as measured by a dynamic light scattering method.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidylethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety within the molecule, and sphingolipid which does not contain a phosphoric acid moiety within the molecule. In the present invention, the term "lipids other than phospholipids" also encompasses derivatives of lipids other than phospholipids in which modifications have been made to the lipids other than phospholipids.

In the case where the lipids other than phospholipids contain a basic functional group, for example, in the case where the lipids other than phospholipids are a material where a compound having a basic functional group is bonded to a lipid, the lipid is referred to as a cationized lipid. The cationized lipid becomes capable of modifying, for example, the membrane of the liposome and therefore can enhance the adhesiveness to cells which are the target sites.

Examples of cholesterols include cholesterol which contains cyclopentahydrophenanthrene as a basic skeleton whose carbon atoms are partially or completely hydrogenated and derivatives thereof. Specific examples of cholesterols include, but are not particularly limited to, cholesterol. When the average particle size decreases to 100 nm or less, the curvature of the lipid membrane becomes higher. Since the deformation of the membrane arranged within the liposome also increases, a water-soluble drug becomes more susceptible to leakage. However, as a means for suppressing leakage properties, it is effective to add cholesterol or the like in order to fill the deformation of the membrane caused by the lipid (membrane-stabilizing effect).

The addition of cholesterol into liposome compositions is expected to lower the fluidity of the liposome membrane by filling membrane gaps of liposomes, or the like. Generally, it has been desired that the content of cholesterol in liposomes is usually an amount of up to about 50 mol % of the total moles of lipid components (total lipid).

In the present invention, in total moles of lipid components in the liposome composition (total lipid contained in the liposome composition), the content of cholesterol is preferably 10 to 35 mol %, more preferably 15 to 25 mol %, and still more preferably 17 to 21 mol %.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not approved for use as an intravenous injection in pharmaceutical applications, for example, a surfactant or the like.

The liposome preferably contains hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in a combination of two or more thereof.

Among these, from the viewpoint of retentivity in blood of a formulation, preferred are polyethylene glycols, polyglycerols, and polypropylene glycols, and more preferred are polyethylene glycol (PEG), polyglycerol (PG), and polypropylene glycol (PPG). Polyethylene glycol (PEG) is most commonly used and is preferable due to having an effect of improving the retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome, it is preferable to use a lipid modified by PEG (PEG-modified lipid), together with the main lipid contained in the liposome. Specific examples of the PEG-modified lipid include 1,2-distearoyl-3-phosphatidylethanolamine-PEG (DSPE-PEG; manufactured by Nippon Oil & Fats Co., Ltd.; specifically 1,2-distearoyl-3-phosphatidylethanolamine-PEG2000, or 1,2-distearoyl-3-phosphatidylethanolamine-PEG5000 is preferable) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome, preferred is a lipid combination of hydrogenated soybean phosphatidylcholine (a main lipid contained in the liposome) and 1,2-distearoyl-3-phosphatidylethanolamine-PEG (a lipid used in combination with the main lipid).

The liposome preferably does not contain an anionic polymer (polyanion). In the present invention, since it is possible to control the release ability by means of an osmotic pressure of an inner water phase, there are advantages in that general versatility is excellent, and drugs which can be used in liposomes are not limited.

(Method for Producing Liposome)

The method for producing a liposome according to the present invention is a method for producing a liposome, including a stirring step of stirring a mixed liquid containing an oil phase in which at least one lipid is dissolved in an organic solvent and a water phase, and an evaporating step of evaporating an organic solvent from the mixed liquid, in which the condensed organic solvent is removed by passing a gas having a temperature not higher than the dew point of the solvent in the evaporating step.

The emulsifying step of emulsifying mixed lipids dissolved in an organic solvent to form a liposome, without a drying and solidifying step, is not limited as long as it is a step of emulsification, but it is preferably a step of applying a high shearing force and performing microparticulation in an emulsifying step including an organic solvent. If necessary, evaporation (desolvation) of the organic solvent used in the emulsifying step may be carried out to form a liposome.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is spontaneously miscible with water. Specific examples of the water-soluble organic solvent include alcohols such as methanol, ethanol, n-propanol, isopropanol, n-butanol, isobutanol, and t-butanol; glycols such as glycerin, ethylene glycol, and propylene glycol; and polyalkylene glycols such as polyethylene glycol. Among these, preferred are alcohols. The alcohol is preferably at least one selected from ethanol, methanol, 2-propanol, or t-butanol, more preferably at least one selected from ethanol, 2-propanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be about 90:10 to 20:80 and preferably about 70:30 to 25:75 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is in the range of preferably about 4 to 10 and more preferably about 6 to 9. The ester-based organic solvents may contain physiologically active substances or the like such as various drugs which are soluble in these solvents.

The concentration of the lipid is not particularly limited and may be appropriately adjusted, but it may be 40 g/L to 250 g/L, preferably 100 g/L to 200 g/L in terms of a solution where a mixed liquid of a water-soluble organic solvent and an ester-based organic solvent serves as a solvent.

(Water Phase)

As a water phase (aqueous solution) where the membrane components are dispersed when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of a body fluid is preferably used and examples thereof include phosphate buffer, Tris buffer, citrate buffer, acetate buffer, and Good's buffer. The pH of the water phase is not particularly limited, and it may be 5.0 to 9.0 and preferably 7.0 to 8.0. For example, a phosphate buffer (for example, pH=7.4) is preferably used. The aqueous solution finally contained in the inner water phase of the liposome may be an aqueous solution for dispersing the membrane components when producing the liposome, or may be water, physiological saline, various buffers, an aqueous solution of sugars or a mixture thereof which is newly added. The water used as a water phase (aqueous solution) is preferably free from impurities (dust, chemicals, or the like).

(Emulsifying Step)

In the emulsifying step, an oil phase where at least one lipid has been dissolved in an organic solvent and a water phase are mixed to prepare an aqueous solution containing lipids, which is then emulsified by stirring. An oil phase where lipids have been dissolved in an organic solvent and a water phase are mixed, stirred and emulsified to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated during the course of the stirring-emulsification to form a liposome.

As a method of stirring, ultrasonic waves or mechanical shearing force is used for particle miniaturization. In addition, extruder processing of allowing to pass through a filter having a certain pore size or microfluidizer processing may be carried out for uniformity of the particle sizes. Use of an extruder or the like can result in deformation of secondarily formed multivesicular liposomes into univesicular liposomes. In the present invention, it is preferred from the viewpoint of simplification of the production process that a liposome of a state that has no drug loading is used in the next step without extrusion processing.

Emulsification may be carried out by stirring in a tank. The capacity of the tank is not particularly limited, but from the viewpoint of large scale production being favorable, it is preferably 10 L or more and 100 L or less and more preferably 20 L or more and 100 L or less.

When carrying out the emulsification, a mixture can be circulated using a pump, which may be a turbo-type pump (a centrifugal pump, a diagonal flow pump, or an axial flow pump), a positive displacement reciprocating pump (a piston pump, a plunger pump, or a diaphragm pump), a positive displacement rotary pump (a gear pump, a vane pump, or a screw pump), a tube pump, or the like. Among them, a tube pump or diaphragm pump having no sliding surfaces may be preferably used. Particularly preferred is a diaphragm pump that can easily secure a large flow rate.

For emulsification, it is preferable to stir a mixture in a tank using an emulsifying apparatus. Examples of the emulsifying apparatus that can be used include an impeller type, a sawtooth blade type, a closed rotor type, a rotor/stator type, a static mixer type, a colloid mill type, and a high-pressure homogenizer type. Among them, preferred is an impeller type, a sawtooth type, a closed rotor type, or a rotor/stator type which is suitable for batch processing in a tank.

Particularly preferred is a rotor/stator type which is capable of generating a jet flow in a treatment liquid by high-speed rotation for miniaturization, and capable of sufficiently exerting shear forces between liquid and liquid or liquid and wall surface. As an example, an intermittent jet flow generating type emulsifying apparatus can be used.

In the present invention, an average particle size of a liposome to be prepared can be controlled by arbitrarily selecting the speed and time of stirring. In view of obtaining a liposome having safety and stability, it is preferable to provide shearing at a circumferential speed of 15 m/sec or higher to an aqueous solution containing lipids. Shearing is not limited, and a specific example thereof is shearing at a circumferential speed of preferably 15 m/sec or higher and 35 m/sec or lower, more preferably shearing at a circumferential speed of 20 m/sec or higher and 35 m/sec or lower, and still more preferably shearing at a circumferential speed of 23 m/sec or higher and 30 m/sec or lower.

(Evaporating Step)

The method of the present invention includes an evaporating step of evaporating an organic solvent from a mixed liquid of the stirring step. In the evaporating step, the organic solvent is evaporated from the aqueous solution containing the liposomes obtained in the emulsifying step. The evaporating step includes at least one of a step of forcibly removing a portion or all of the organic solvent derived from the oil phase as an evaporating step and a step of naturally evaporating a portion or all of the organic solvent in the oil phase during the course of stirring-emulsification.

The method of evaporating an organic solvent in the evaporating step is not particularly limited as long as it is a method of removing the condensed organic solvent by passing a gas having a temperature not higher than the dew point of a solvent. The solvent in "dew point of a solvent" means the total solvent in a mixed liquid, including an organic solvent and water.

Preferably, the stirring step and the evaporating step are carried out in a tank, and the ratio A/B of length A of the widest portion of the liquid horizontal plane of the mixed liquid in the tank at the start of the evaporating step to length B of the deepest portion of the liquid depth is 2 or more, more preferably 3 or more, still more preferably 3.5 or more, and particularly preferably 4 or more.

Preferably, the stirring step and the evaporating step are carried out in a tank, and the ratio C/D of length C of the widest portion of the horizontal plane of the gas space in the tank at the start of the evaporating step to length D of the longest portion of the height of the gas space is 2 or more, more preferably 3 or more, still more preferably 3.5 or more, and particularly preferably 4 or more at the start of desolvation.

The gas space as used herein refers to a space occupied by the gas flowing in a horizontal direction on the liquid surface. That is, the height of the space may exhibit a local height variation due to the shape of the lid at the top of the tank container. The term "space occupied by the gas flowing in a horizontal direction on the liquid surface" refers to a space occupied by the gas in air flow state, without taking into account such a local height variation.

A sufficient heat transfer area and a sufficient gas-liquid interfacial area can be ensured by setting A/B to 2 or more and/or C/D to 2 or more as described above, so that it becomes possible to achieve a more rapid desolvation.

Preferably, the evaporating step may be carried out while stirring using a centrifugal stirrer. In order to achieve rapid desolvation, it is effective to improve a heat transfer coefficient. As a means for this purpose, it is considered to strengthen the stirring. However, if the stirring is strengthened, air bubbles will be generated by air entrainment. In particular, in the case of using a tank having A/B of 2 or more and/or C/D of 2 or more, the water depth becomes shallow and consequently air entrainment becomes severe. It has now been found that the use of a centrifugal stirrer makes it possible to suppress foaming and strengthen the stirring. That is, the use of a centrifugal stirrer is preferable from the viewpoint of rapid desolvation.

The structure of the centrifugal stirrer is a rotating body which forms a flow path by connecting an inlet port near the rotating shaft and a discharge port distant from the rotating shaft. The principle of stirring is as follows: (1) Stirrer is rotated, (2) Centrifugal force acts on the flow path, (3) Fluid is discharged in the transverse direction, (4) Vertical flow path becomes a negative pressure, and (5) Negative pressure suction flow is generated in the downward direction.

An M-Revo (registered trademark, manufactured by Medech Co., Ltd.) or the like may be used as the centrifugal stirrer. A schematic diagram of M-Revo is shown in FIG. 1 (quoted from the home page of the manufacturer). When M-Revo is rotated, a centrifugal force is generated at the discharge port (a), and the fluid is discharged in the transverse direction from (a). As a result, a suction force is generated in the inlet port (b), and a tornado-like vortex flow (c) is generated. A negative pressure is generated in the vertical flow path, a negative pressure suction flow occurs in the downward direction, and a "push→pull" flow is generated. A pulsation (pulse) is transmitted from the M-Revo to the stirring flow and the stirring flow propagates throughout.

The dimension of the rotor of the centrifugal stirrer is preferably 70 to 200 mm, more preferably 80 to 150 mm in diameter, and it is preferable to have a plurality of (for example, 2 to 10) discharge ports in the circumferential portion. The discharge rate coefficient (total opening area of the discharge ports×circumferential length), which is an index of the stirring capacity of the rotor, is preferably 60 $cm^3$ to 6,000 $cm^3$, and more preferably 200 $cm^3$ to 2,000 $cm^3$.

The rotation speed of the centrifugal stirrer is preferably 100 to 1,500 rpm (rotation/minute), more preferably 200 to 1,000 rpm, and still more preferably 300 to 800 rpm.

In the case where the radius of the tank is taken to be 1, it is preferable with respect to the eccentricity that the rotating shaft is located at a position of 0 (center of tank=0) to 0.8 from the center of the tank, but it is necessary that the rotor and the inner wall of the tank are not in contact with each other.

Preferably, in the evaporating step, the gas can be sucked into the container from the central portion of the upper portion of the container, and the gas and the condensed organic solvent can be discharged from the peripheral portion of the upper portion of the container. As mentioned above, blowing air in the direction from the center to the outer periphery is preferable from the viewpoint of rapid desolvation.

In the present invention, in the step of evaporating an organic solvent, it is preferred that the concentration of an organic solvent contained in an aqueous solution containing liposomes is to be 15 mass % or less within 30 minutes since the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes obtained by the present invention may be subjected to post-processing such as centrifugation, ultrafiltration, dialysis, gel filtration, or freeze-drying, for removal of components that had not been included in the liposomes, or adjustment of a concentration and an osmotic pressure.

Particle sizes of the resulting liposomes can be made uniform by using dialysis, filtration, extrusion processing, or the like. In the method for producing a liposome according to the present invention, it is preferred that empty liposomes are prepared in a state where a drug is not loaded, without subjection to extrusion processing. Moreover, if it is desired to separate the drug encapsulated in liposomes from the drug not encapsulated in liposomes, centrifugation, dialysis, gel filtration, or the like may be employed.

(Apparatus for Producing Liposome)

The apparatus for producing a liposome according to the present invention is an apparatus for producing a liposome, including a tank, a stirrer, and a jacket, in which the cross-section of the space in the tank has a circular shape, the size of the circle in the cross-section is variable depending on the height of the tank, the stirrer is inserted into the tank from the center of the lid at the top of the tank, the jacket is provided around the tank to control the temperature in the tank, one or more inlet ports for sucking gas into the tank are provided at the central portion of the lid at the top of the tank, and one or more outlet ports for discharging the gas and condensed organic solvent from the tank are provided at the periphery of the lid at the top of the tank. The insertion position of the stirrer may be eccentric from the center of the tank within the range of eccentricity described in paragraph 0054 of the present specification.

Figure 2:
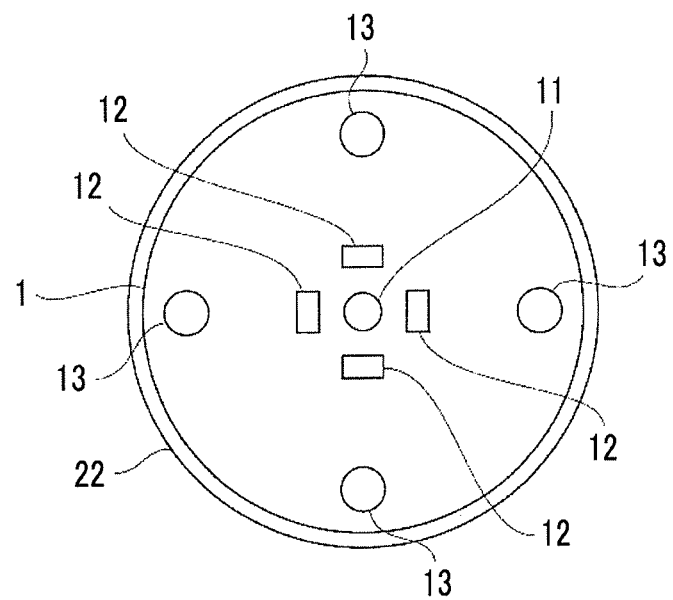
FIG. 2 shows a top view of a configuration example of an apparatus for producing a liposome according to the present invention.
Figure 3:
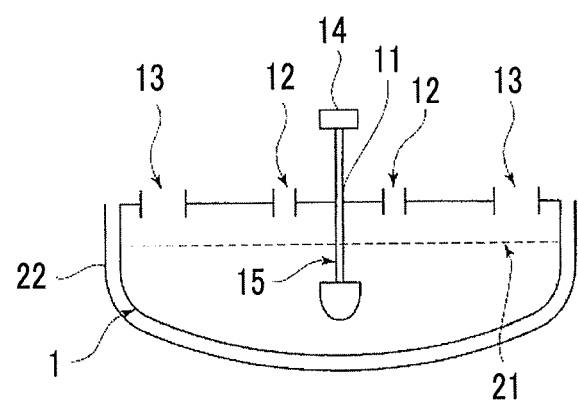
FIG. 3 shows a cross-sectional view of a configuration example of an apparatus for producing a liposome according to the present invention.

FIG. 2 shows a top view of an example of the configuration of the apparatus for producing a liposome according to the present invention, and FIG. 3 shows a cross-sectional view thereof.

The shape of the tank 1 when viewed from the top is substantially a circular shape, that is, the cross-section of the space in the tank has a substantially circular shape in which the size of the circle represented by the cross-section of the space in the tank may vary depending on the height of the tank. In the example shown in FIG. 3, the size of the circle of the cross-section in the top half of the tank is almost constant, whereas the size of the circle of the cross-section in the bottom half of the tank varies depending on the height of the tank, so that the size of the circle of the cross-section is small for a region where the height of the tank is low.

A stirrer 15 is inserted into the tank from a center 11 of the lid at the top of the tank. The stirrer 15 is operated by a stirring means 14.

A jacket 22 for controlling the temperature in the tank is provided around the tank 1.

Four inlet ports 12 for sucking gas into the tank are provided in the central portion of the lid (adjacent region around the center 11) at the top of the tank 1. Four outlet ports 13 for discharging gas and condensed organic solvent from the tank are provided in the peripheral portion of the lid (region adjacent to the outer periphery of the lid) at the top of the tank 1.

The reference numeral 21 in FIG. 3 indicates the liquid surface (gas-liquid interface) when the liquid is introduced.

(Drug Loading Step)

The liposome obtained by the method of the present invention can encapsulate a drug. In the drug loading step of encapsulating the drug, in the case of encapsulating a water-soluble drug in the liposomes, the drug can be encapsulated in the inner water phase of the liposome by a method of dissolving the drug in an aqueous medium capable of performing hydration and swelling, followed by heating at a temperature higher than or equal to the phase transition temperature, and sonication or extrusion. A drug may also be encapsulated in an inner water phase by dissolving the drug in the water phase at a time of lipid emulsification.

The drug contained in the liposome may be any water-soluble drug that can be encapsulated in liposomes, and specific examples thereof include, but are not limited to, water-soluble materials having a physiological activity or a pharmacological activity such as enzymes, proteins, peptides, nucleic acids (DNA, mRNA, siRNA, miRNA), low-molecular weight compounds, sugars (oligosaccharides and polysaccharides), polymer compounds, antitumor agents, antimicrobial agents, contrast agents, antioxidants, anti-inflammatory agents, whitening agents, humectants, and hair growing agents. In the case of using a liposome as a carrier for a drug delivery system, the water-soluble drug is preferably a low-molecular weight compound from the viewpoint of stability.

Specific examples of the water-soluble drug include anti-cancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a vinca alkaloid-based anticancer agent such as vincristine or vinblastine, a bleomycin-based anticancer agent such as bleomycin, a sirolimus-based anticancer agent such as sirolimus, and a metabolic antagonist such as methotrexate, fluorouracil, gemcitabine, cytarabine, or pemetrexed. Among these, preferred is a water-soluble drug such as doxorubicin, gemcitabine, or pemetrexed.

The water-soluble drug encapsulated in the liposome is present in a dissolved state in the inner water phase of the liposome. Here, with regard to the dissolved state, it is deemed to be encapsulated as a dissolved state in a case where the amount of the drug filled with respect to the volume of the liposome is below the saturation solubility of the drug in the composition liquid of the inner water phase. Further, even when the amount of the drug filled is above the saturation solubility of the drug, a case where drug crystals are not observed by a cryo-transmission electron microscope (Cryo-TEM) and diffraction patterns attributable to crystal lattice are not observed by X-ray diffraction (XRD) measurement indicates that most of the drug is dissolved due to acceleration of dissolution by a physicochemical environment created by the lipid membrane, partial incorporation of the drug into the lipid membrane or the like, and is deemed to be encapsulated as a dissolved state. In addition, a substance encapsulated by a loading method in which a solid substance is formed inside the liposome and a drug is encapsulated is not in a dissolved state, even when it is a highly water-soluble drug.

The water-soluble drug to be encapsulated in a dissolved state preferably has a solubility in water of 1 mg/ml or more, and more preferably a solubility in water of 10 mg/ml or more.

(Sterile Filtration)

In order to formulate an aqueous solution containing liposomes, obtained by the method for producing a liposome composition according to the present invention, into a pharmaceutical composition, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered using a filter having a sterile pore size (preferably 0.2 µm sterile filter) although there is no particular limitation. Normally, adsorption or aggregation of liposomes onto a sterile filter may occur in the filtration step. However, the present invention has unexpected effects such as little influence in pressure loss or the like when performing filtration, since liposomes having a specific average particle size and a uniform particle size distribution are obtained.

To prevent an effect of deformation of liposomes on the average particle size, the sterile filtration step and the below-described aseptic filling step are preferably carried out at a temperature lower than or equal to the phase transition temperature of the lipids constituting the liposome. For example, in the case where the phase transition temperature of the lipid is around 50° C., the sterile filtration step and the below-described aseptic filling step are carried out at a temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome composition suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a pharmaceutical composition containing liposomes. In connection with the route of administration, the pharmaceutical composition may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and EDTA. Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The pharmaceutical composition may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the pharmaceutical composition preferably contains ammonium sulfate, L-histidine, purified sucrose, sodium hydroxide, hydrochloric acid, or the like.

The container in which a pharmaceutical composition is filled is not particularly limited, and it is preferably made out of a material having low oxygen permeability. Examples of the container include a plastic container, a glass container, and a bag made out of a laminate film having an aluminium foil, an aluminium-deposited film, an aluminium oxide-deposited film, a silicon oxide-deposited film, a polyvinyl alcohol, an ethylene-vinyl alcohol copolymer, a polyethylene terephthalate, a polyethylene naphthalate, a polyvinylidene chloride, or the like as a gas barrier layer. If necessary, light may be shielded by adopting a bag or the like using a colored glass, an aluminium foil, an aluminium-deposited film, or the like.

In the container in which a pharmaceutical composition is filled, in order to prevent oxidation by oxygen present in the space of the container, it is preferable to replace the gases in the container space and drug solution with inert gases such as nitrogen. For example, an injection solution is bubbled with nitrogen, whereby the filling of the injection solution into a container can be carried out under a nitrogen atmosphere.

The administration method of a pharmaceutical composition is preferably a parenteral administration. For example, intravenous injections such as intravenous drip, intramuscular injection, intraperitoneal injection, subcutaneous injection, intraocular injection, or intrathecal injection may be selected. The specific administration method of a liposome composition includes, for example, a syringe and administration by intravenous drip.

The dose of a drug contained in the pharmaceutical composition is usually selected from a range of 0.01 mg to 100 mg/kg body weight/day. However, the liposome composition of the present invention is not limited to such a dose.

EXAMPLES

Hereinafter, the present invention will be described in detail with reference to Examples. However, the present invention is not limited to such Examples.

Example 1 a) Preparation of Equipment

A tank having a structure shown in FIG. 2 and FIG. 3 was prepared.

The tank was equipped with an M-Revo (registered trademark, manufactured by Medech Co., Ltd.) which was used as a centrifugal stirrer.

The shape of the tank is such that A/B is 4 and C/D is 4 in the case where 25.5 kg of water and 7.8 kg of ethanol (about 33.3 L in total) are introduced.

b) Preparation of Test Solution

As the test solution, 25.5 kg of water and 7.8 kg of ethanol were used.

c) Desolvation 25.5 kg of water and 7.8 kg of ethanol were introduced into the tank. 80° C. hot water was circulated in the jacket of the tank such that the temperature was increased. When the internal temperature of the tank reached 70° C., the evaporation process was started. Stirring with a centrifugal stirrer was started and simultaneously, air at a temperature of 20° C. was blown at an air flow rate of 4.0 Nm$^3$/min.

The rotor of the centrifugal stirrer has a diameter of 10 cm and has six discharge ports with a diameter of 1 cm in the circumferential portion. The rotation speed of the centrifugal stirrer was set to 600 rpm. The amount of eccentricity was such that the rotating shaft was positioned 65 mm external from the center of the tank. The discharge rate coefficient (total opening area of discharge ports×circumferential length), which is an index of the stirring capacity of the rotor, was 591 cm$^3$.

Air was sucked from the inlet port at the top of the tank and discharged from the outlet port at the top of the tank to thereby blow air in a direction from the center to the outer periphery.

After 10 minutes, the evaporating step was completed, and the liquid was recovered from the tank. The mass of the recovered liquid was measured and the residual concentration of ethanol was measured by gas chromatography to thereby calculate the evaporation amount of water and ethanol during the evaporation process. The results of the above calculation are shown in Table 1. The dew point (calculated value) was 33° C.

Comparative Example 1

The evaporation process was carried out in the same manner as in Example 1, except that the blowing air temperature was set to 50° C. by a heating device. As the heating device, a heat exchanger in which hot water passes through the primary side and a carrier (air or nitrogen) passes through the secondary side was used.

The calculated results of the evaporation amount of water and the evaporation amount of ethanol are shown in Table 1. The dew point (calculated value) was 31° C.

Comparative Example 2

The evaporation process was carried out in the same manner as in Example 1, except that the air flow rate was set to 12 Nm$^3$/min.

The calculated results of the evaporation amount of water and the evaporation amount of ethanol are shown in Table 1. The dew point (calculated value) was 14° C.

Example 2

The evaporation process was carried out in the same manner as in Example 1, except that the shape of the tank was such that A/B was 1 and C/D was 4 in the case where 25.5 kg of water and 7.8 kg of ethanol (about 33.3 L in total) were introduced.

The calculated results of the evaporation amount of water and the evaporation amount of ethanol are shown in Table 1. The dew point (calculated value) was 26° C.

Example 3

The evaporation process was carried out in the same manner as in Example 1, except that the shape of the tank was such that A/B was 4 and C/D was 2 in the case where 25.5 kg of water and 7.8 kg of ethanol (about 33.3 L in total) were introduced.

The calculated results of the evaporation amount of water and the evaporation amount of ethanol are shown in Table 1. The dew point (calculated value) was 27° C.

Example 4

The evaporation process was carried out in the same manner as in Example 1, except that the direction of air blowing was set to one direction.

The calculated results of the evaporation amount of water and the evaporation amount of ethanol are shown in Table 1. The dew point (calculated value) was 27° C.

Example 5

The evaporation process was carried out in the same manner as in Example 1, except that a paddle type stirrer (blade diameter: 100 mm) was used instead of the centrifugal stirrer and the rotation speed was set to 350 rpm.

The calculated results of the evaporation amount of water and the evaporation amount of ethanol are shown in Table 1. The dew point (calculated value) was 30° C.

In the foregoing Examples and Comparative Examples, the rate of desolvation was determined according to the following standards. Ratings A to C are acceptable levels.

A: The evaporation amount of ethanol was 100 g/min or more.

B: The evaporation amount of ethanol was 70 g/min or more and less than 100 g/min.

C: The evaporation amount of ethanol was 50 g/min or more and less than 70 g/min.

The dew point of each example was calculated by the following method.

1) Vapor partial pressures of water and ethanol were calculated from the actual values of evaporation amount (water), evaporation amount (ethanol) and air flow rate using the state equation of gas, and the total of the calculated vapor partial pressures was taken as the total pressure of the vapor.

2) From the total vapor pressure calculated in 1) and the introduced mole fraction of the liquid composition, the dew point in the state was calculated using Antoine equation and Wilson equation in vapor-liquid equilibrium.

The details of the method for calculating vapor-liquid equilibrium are described in the following literatures.

"Theory and Calculation of Phase Equilibrium for the Separation", pp. 75 to 76, written by Shuzo Ohe (Kodansha Ltd., 2012)

"Vapor-Liquid Equilibrium Data Collection", p 216, written by Shuzo Ohe (Kodansha Ltd., 1988).

TABLE 1

|  | Example 1 | Comparative Example 1 | Comparative Example 2 | Example 2 | Example 3 | Example 4 | Example 5 |
| --- | --- | --- | --- | --- | --- | --- | --- |
| Heating device | No | Yes | No | No | No | No | No |
| Tank-shaped liquid part A/B | 4 | 4 | 4 | 1 | 4 | 4 | 4 |
| Tank-shaped gas flow part C/D | 4 | 4 | 4 | 4 | 2 | 4 | 4 |
| Air blowing | From center to outer periphery | From center to outer periphery | From center to outer periphery | From center to outer periphery | From center to outer periphery | One direction | From center to outer periphery |

TABLE 1-continued

| | Example 1 | Comparative Example 1 | Comparative Example 2 | Example 2 | Example 3 | Example 4 | Example 5 |
|---|---|---|---|---|---|---|---|
| Stirrer | Centrifugal | Centrifugal | Centrifugal | Centrifugal | Centrifugal | Centrifugal | Paddle type |
| Air flow rate $Nm^3$/min | 4.0 | 4.0 | 12 | 4.0 | 4.0 | 4.0 | 4.0 |
| Blowing air temperature ° C. | 20 | 50 | 20 | 20 | 20 | 20 | 20 |
| Evaporation amount (water) g/min | 182 | 187 | 185 | 127 | 135 | 130 | 85 |
| Evaporation amount (ethanol) g/min | 106 | 110 | 107 | 75 | 78 | 76 | 51 |
| Dew point ° C. | 33 | 31 | 14 | 26 | 27 | 27 | 30 |
| Desolvation rate | A | A | A | B | B | B | C |
| Capital investment burden | Acceptable | Non-acceptable | Non-acceptable | Acceptable | Acceptable | Acceptable | Acceptable |

As can be seen from Table 1, in Examples 1 to 5 of the present invention, it was possible to achieve the desolvation rate that could be tolerated under the conditions without a capital investment burden.

Example 6 a) Preparation of Emulsification Equipment

Figure 4:
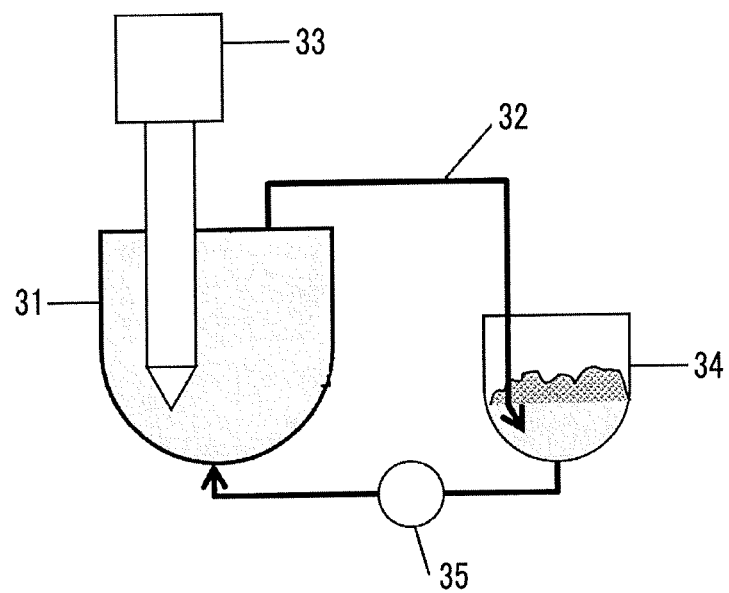
FIG. 4 shows a configuration of an emulsifying apparatus used in the Examples.

The emulsification equipment was prepared by combining a circulation path 32 (the capacity of the circulation path is 6 L) including an intermittent jet flow generating type emulsifying apparatus 33 having a rotating part with a slit outer diameter of 90 mm (CLEARMIX (registered trademark) manufactured by M Technique Co., Ltd.), an emulsifying tank 31 with a full-water capacity of 26 L, a defoaming tank 34, and a circulating pump 35 (direct-acting diaphragm pump model EJL1500S12 manufactured by Nikkiso-LEWA GmbH) as shown in FIG. 4. The capacity of the circulation path is the capacity of the entire circulation path including the defoaming tank.

b) Preparation of Oil Phase

Hydrogenated soybean phosphatidylcholine, cholesterol and N-(carbonyl-methoxypolyethylene glycol 2000)-1,2-distearoyl-sn-glycero-3-phosphoethanolamine sodium salt (hereinafter referred to as DSPE-PEG) were mixed to a molar ratio of 57/38/5, and then an organic solvent (ethanol) was added thereto, followed by warming to 70° C. and dissolution of the lipids to prepare an oil phase. Here, the oil phase was prepared such that the lipid concentration in the oil phase was 70 mmol/L.

c) Preparation of Water Phase 177 mmol/L of an aqueous ammonium sulfate solution was prepared and was then prepared as a water phase in an emulsifying tank.

d) Emulsification

The water phase prepared in c) was heated to 70° C. The oil phase prepared in b) was added so that the volume ratio of water phase/oil phase=8/3 was obtained while operating an emulsifying apparatus at a circumferential speed of 15 m/s and operating a circulation pump at a flow rate of 20 L/min. The total amount of the liquid after the addition was 32 L. After the emulsifying tank was fully hydrated, the overflowed 6 L circulated through the circulation path including the defoaming tank. The internal pressure of the emulsifying tank was set to 30 kPa. In this state, the rotation of the emulsifying apparatus was increased to a circumferential speed of 30 m/sec, followed by stirring for 30 minutes.

e) Desolvation

The emulsion prepared in d) was quickly transferred to a desolvation tank (which is the same as that used in Example 1). 80° C. hot water was circulated in the jacket of the tank, so that the evaporation process was started as the temperature warmed. At the same time as starting the stirring in the centrifugal stirrer (the same conditions as in Example 1), 20° C. air was blown at a rate of 4.0 $Nm^3$/min. After 10 minutes, the temperature of the hot water in the jacket was modified to 60° C. and the air flow rate was changed to 3.0 $Nm^3$/min. After 60 minutes from the start, the rotation speed of the centrifugal stirrer was changed to 450 rpm and the air flow rate was changed to 1.4 $Nm^3$/min. After 4 hours from the start, the rotation speed of the centrifugal stirrer was changed to 300 rpm. The evaporation process was completed after 6 hours from the start, and the liposome liquid was recovered from the tank. The dew point (calculated value) was 33° C. at the start of desolvation.

Example 7

The liposome liquid was prepared and recovered in the same manner as in Example 6, except that a paddle type stirrer (blade diameter: 100 mm) was used instead of the centrifugal stirrer and the rotation speed was set to 350 rpm at the start of desolvation and 150 rpm after 60 minutes from the start of the desolvation. The dew point (calculated value) was 33° C. at the start of desolvation.

(Measurement of Average Particle Size of Liposomes by Dynamic Light Scattering Method)

The liposome liquids prepared in Examples 6 and 7 were 40-fold diluted with pure water to obtain samples for measuring an average particle size. The average particle size of the samples for measuring an average particle size was measured in terms of volume average particle size using a particle size analyzer FPAR-1000AS (manufactured by Otsuka Electronics Co., Ltd.).

The measurement results are shown in Table 2. As shown in Table 2, although it is possible to produce liposomes using any one of a centrifugal stirrer or a paddle type stirrer, it was found that the use of a centrifugal stirrer is preferable since liposomes having a smaller average particle size can be produced as in Example 6 using a centrifugal stirrer. Because Example 7 employs a lipid (DSPE-PEG) which readily generates bubbles, the amount of bubbles increases and therefore the desolvation tends to be delayed in the case of using a paddle type stirrer.

TABLE 2

| | Example 6 | Example 7 |
|---|---|---|
| Heating device | No | No |
| Tank-shaped liquid part A/B | 4 | 4 |
| Tank-shaped gas flow part C/D | 4 | 4 |
| Air blowing | From center to outer periphery | From center to outer periphery |

TABLE 2-continued

|  | Example 6 | Example 7 |
| --- | --- | --- |
| Stirrer | Centrifugal | Paddle type |
| Air flow rate Nm$^3$/min | 4.0 to 2.0 | 4.0 to 2.0 |
| Blowing air temperature ° C. | 20 | 20 |
| Dew point ° C. (at start of desolvation) | 33 | 33 |
| Average particle size nm | 59 | 81 |

Example 8

Preparation of Drug-Encapsulated Liposomes

With respect to the non-drug encapsulated liposomes prepared in Example 6, the lipid concentration of the liposome liquid was concentrated to a range of 120 to 150 mmol/L by tangential flow filtration, while the outer water phase of the liposome was replaced with a 0.09 mass % aqueous sodium chloride solution. A drug solution prepared by heating to dissolve gemcitabine hydrochloride in a phosphate buffer solution was added thereto. The mixture was heated at about 70° C. for 30 minutes and then cooled to room temperature. Thereafter, the drug-liposome mixture was filtered through a sterilization filter having a pore size of 0.2 µm. Further, the drug-liposome mixture was purified by dialysis against a 9.4 mass % sucrose/10 mmol/L-histidine aqueous solution by tangential flow filtration to remove non-encapsulated gemcitabine. This was followed by filtration of liposomes through a sterilizing filter having a pore size of 0.2 µm to obtain a solution of sterile gemcitabine-encapsulated liposomes having an average particle size of 69 nm. According to the present invention, it was confirmed that liposomes having a single dispersion peak and a small average particle size of 100 nm or less usable for medical applications can be produced.

INDUSTRIAL APPLICABILITY

According to the present invention, liposomes can be produced on large scale production. The liposomes produced by the present invention can be applied to medicines, cosmetics, foods, or the like, and are particularly useful for medical applications.

EXPLANATION OF REFERENCES

1: tank
11: center
12: inlet port
13: outlet port
14: stirring means
15: stirrer
21: liquid surface
22: jacket
31: emulsifying tank
32: circulation path
33: emulsifying apparatus
34: defoaming tank
35: pump

What is claimed is:

1. A system for producing a liposome, comprising emulsification equipment and desolvation equipment,
   wherein the desolvation equipment comprises
      a tank;
      a stirrer; and
      a jacket,
      wherein the cross-section of the space in the tank has a circular shape, the size of the circle in the cross-section is variable depending on the height of the tank and the diameter of the cross-section of the space in the tank is longer than the height of the tank, the stirrer is inserted into the tank from the center of a lid at the top of the tank, the jacket is provided around the tank to control the temperature in the tank, one or more inlet ports for sucking gas into the tank are provided at the central portion of the lid at the top of the tank, and one or more outlet ports for discharging the gas and condensed organic solvent from the tank are provided at a peripheral portion of a gas space above a liquid in the tank comprising an organic solvent or organic solvents, and wherein the emulsification equipment comprises an emulsifying tank and an emulsifying apparatus.

2. The system for producing a liposome according to claim 1, wherein the capacity of the tank is within a range of 10 L or more and 100 L or less.

3. The system for producing a liposome according to claim 1,
   wherein a stirring step and an evaporating step are carried out in the tank, and the ratio A/B of length A of the widest portion of a liquid horizontal plane of the liquid comprising the organic solvent in the tank at the start of the evaporating step to length B of a deepest portion of the liquid depth is 2 or more.

4. The system for producing a liposome according to claim 2,
   wherein a stirring step and an evaporating step are carried out in the tank, and the ratio A/B of length A of the widest portion of a liquid horizontal plane of the liquid comprising the organic solvent in the tank at the start of the evaporating step to length B of a deepest portion of the liquid depth is 2 or more.

5. The system for producing a liposome according to claim 1,
   wherein a stirring step and an evaporating step are carried out in the tank, and the ratio C/D of length C of the widest portion of a horizontal plane of the gas space in the tank at the start of the evaporating step to length D of the longest portion of the height of the gas space is 3 or more,
   wherein the gas space is a space occupied by the gas flowing in a horizontal direction on a liquid surface.

6. The system for producing a liposome according to claim 2,
   wherein a stirring step and an evaporating step are carried out in the tank, and the ratio C/D of length C of the widest portion of a horizontal plane of the gas space in the tank at the start of the evaporating step to length D of the longest portion of the height of the gas space is 3 or more,
   wherein the gas space is a space occupied by the gas flowing in a horizontal direction on a liquid surface.

7. The system for producing a liposome according to claim 3,
   wherein the stirring step and the evaporating step are carried out in the tank, and the ratio C/D of length C of the widest portion of the horizontal plane of the gas space in the tank at the start of the evaporating step to length D of the longest portion of the height of the gas space is 3 or more,
   wherein the gas space is a space occupied by the gas flowing in a horizontal direction on a liquid surface.

8. The system for producing a liposome according to claim 4, wherein the stirring step and the evaporating step are carried out in the tank, and the ratio C/D of length C of the widest portion of the horizontal plane of the gas space in the tank at the start of the evaporating step to length D of the longest portion of the height of the gas space is 3 or more, wherein the gas space is a space occupied by the gas flowing in a horizontal direction on a liquid surface.

9. The system for producing a liposome according to claim 1, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

10. The system for producing a liposome according to claim 2, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

11. The system for producing a liposome according to claim 3, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

12. The system for producing a liposome according to claim 4, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

13. The system for producing a liposome according to claim 5, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

14. The system for producing a liposome according to claim 6, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

15. The system for producing a liposome according to claim 7, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

16. The system for producing a liposome according to claim 8, wherein the stirrer has 2 to 10 discharge ports, a discharge rate coefficient indicated by a total opening area of the discharge ports multiplied by a circumferential length of a rotor of the stirrer is 60 cm$^3$ to 6,000 cm$^3$, and the rotation speed of the stirrer is 100 to 1,500 rpm.

17. The system for producing a liposome according to claim 1, wherein the one or more inlet ports comprises one to four inlet ports for sucking gas into the tank are provided at a central portion of the lid at the top of the tank.

18. The system for producing a liposome according to claim 1, wherein the one or more outlet ports comprises one to four outlet ports for discharging the gas and condensed organic solvent from the tank are provided at a peripheral portion of a gas space above a liquid surface of a liquid comprising the organic solvent is contained in the tank.

19. The system for producing a liposome according to claim 1, wherein the emulsification equipment further comprises a defoaming tank and a circulation path.

20. The system for producing a liposome according to claim 19, wherein the emulsifying tank is connected with the defoaming tank through the circulation path.

* * * * *